(12) United States Patent
Gillies et al.

(10) Patent No.: US 11,331,133 B2
(45) Date of Patent: May 17, 2022

(54) ORTHOPAEDIC REDRESSING DEVICE (71) Applicant: MatOrtho Limited, Leatherhead (GB)

(72) Inventors: Ronald Mark Gillies, Enmore (AU); Simon Collins, Leatherhead (GB)

(73) Assignee: MEDICAL DEVICE RESEARCH AUSTRALIA PTY LTD, Enmore (AU)

( * ) Notice: Subject to any disclaimer, the term of this patent is extended or adjusted under 35 U.S.C. 154(b) by 444 days.

(21) Appl. No.: 16/308,588

(22) PCT Filed: Jun. 7, 2017

(86) PCT No.: PCT/GB2017/051642
§ 371 (c)(1),
(2) Date: Dec. 10, 2018

(87) PCT Pub. No.: WO2017/212254
PCT Pub. Date: Dec. 14, 2017

(65) Prior Publication Data
US 2019/0151004 A1 May 23, 2019

(30) Foreign Application Priority Data
Jun. 10, 2016 (AU) .................... 2016902268

(51) Int. Cl.
*A61B 17/88* (2006.01)
*B24B 5/14* (2006.01)
(Continued)

(52) U.S. Cl.
CPC ............ *A61B 17/8863* (2013.01); *B24B 5/14* (2013.01); *A61F 2002/30332* (2013.01);
(Continued)

(58) Field of Classification Search
CPC ......... B23B 5/165; B23B 5/167; B23B 5/168; A61B 17/7005; A61B 17/8863;
(Continued)

(56) References Cited

U.S. PATENT DOCUMENTS 2,513,228 A 6/1950 Arms et al.
3,020,787 A * 2/1962 Cusick .................... B23B 5/167
408/201

(Continued)

FOREIGN PATENT DOCUMENTS

EP 0891755 A2 1/1999

*Primary Examiner* — Marcela I. Shirsat
(74) *Attorney, Agent, or Firm* — Assouline & Berlowe, P.A.; Peter A. Koziol, Esq.

(57) ABSTRACT

A redressing device (100) for redressing a tapered portion (12) of an orthopaedic implant (10) comprising: a grinding member (110) adapted to engage the tapered portion (12); an adjustable guide element (130) for defining, at least in part, the degree of redressing required for said tapered portion (12) by a user; and a drive shaft (120) for driving movement of said grinding member (110). A device for retaining debris produced during redressing a tapered portion (12) of an orthopaedic implant (12), a surgical kit for redressing a tapered portion (12) of an orthopaedic implant (10) and a method of redressing a tapered portion (12) of an orthopaedic implant (10) are also provided.

10 Claims, 8 Drawing Sheets

(51) Int. Cl.
*A61F 2/30* (2006.01)
*B23B 5/16* (2006.01)
*B23D 37/12* (2006.01)

(52) U.S. Cl.
CPC ............... *B23B 5/165* (2013.01); *B23B 5/167* (2013.01); *B23B 5/168* (2013.01); *B23D 37/12* (2013.01); *Y10T 409/30644* (2015.01); *Y10T 409/306384* (2015.01)

(58) Field of Classification Search
CPC . A61B 17/7011; A61B 17/7026; B23D 37/12; B23D 43/02; Y10T 409/30644; Y10T 409/306384; B24B 5/14; A61F 2002/30332
USPC .............. 29/557; 606/101, 84; 409/179, 138
See application file for complete search history.

(56) References Cited

U.S. PATENT DOCUMENTS

| | | | | |
|---|---|---|---|---|
| 4,895,146 | A | * | 1/1990 | Draenert ................ A61B 10/02 600/567 |
| 5,564,871 | A | | 10/1996 | Andry |
| 7,828,775 | B2 | * | 11/2010 | Okoniewski ....... A61B 17/3421 604/167.01 |
| 2008/0011133 | A1 | * | 1/2008 | Karahalios ............ B23D 21/08 83/13 |
| 2008/0103500 | A1 | | 5/2008 | Chao et al. |
| 2010/0111631 | A1 | * | 5/2010 | Trieu .................... B23D 43/02 409/179 |

* cited by examiner

ORTHOPAEDIC REDRESSING DEVICE

FIELD

This invention relates to an orthopaedic redressing device. More specifically, it relates to a device for redressing a tapered portion of an orthopaedic implant.

BACKGROUND

Modular taper (or trunnion) junctions are a common feature in current total joint replacement design. The use of the taper junction is to allow the ability to interoperatively adjust/modify the joint replacement implant during surgery. In total hip arthroplasty (THA) this modularity allows for a better intraoperative restoration of leg length and control of hip offset via the ability to select and use different femoral head bearing material types (e.g., metal or ceramic) and sizes (e.g., various head diameters and offsets). The use of femoral heads on taper junctions, however, can inevitably lead to micro-motion occurring between the femoral head and its associated taper. The magnitude of this micro-motion will depend on the size of the femoral head used and also the mismatch between the male and female taper angles.

A clinical problem that has become apparent in recent years is the disease commonly referred to as "trunnionosis". Clinically, trunnionosis is defined as the wear of the femoral head-neck interface, due to micro-motion, and has been acknowledged as a source of THA failure. This phenomenon appears to have gained prevalence with newer THA implant designs, in particular metal-on-metal prostheses. Whilst modularity enables a more customised fit for the patient, it may have untoward effects. By way of example, this modularity at times may play a role in increased wear and mechanical insufficiency at the taper, ultimately leading to revision. Trunnionosis is estimated to account for up to 3% of all THA revision procedures. The exact cause of trunnionosis currently remains poorly understood, but contributing factors may include wear between metal-on-metal modular junctions, corrosion and fretting damage, and the release of metal ions or particulate debris from affected components. Additionally, varying implant designs and geometries may have, in some cases, demonstrated a predisposition to excessive fretting and corrosion of the trunnion leading to failure. [1-4]

The generally accepted solution to trunnionosis is revision surgery which represents a costly and risky procedure with a decreased chance of positive outcomes, as blood loss and bone stock is generally compromised. It is not uncommon, however, that if the femoral stem is well fixed it will be left in place and only the metal femoral head may be replaced, such that a new femoral head may be placed onto the damaged male taper. This clearly introduces compromises with respect to the implant, as the original taper was likely highly controlled in terms of its dimensions/tolerances and surface finish. Accordingly, following replacement of the femoral head the implant may be more susceptible to subsequent failure.

Therefore, an alternative or improved approach to the treatment of trunnionosis, or the like, that reduces the risk of subsequent implant failure is required.

SUMMARY

The present invention is broadly directed to a redressing device for redressing a tapered portion of an orthopaedic implant. It would be readily apparent that the redressing device may be used on any orthopaedic implant known in the art that includes a tapered portion, including male and female tapered portions. In this regard, such tapered portions are generally present in many types of orthopaedic implants, such as hip, knee and shoulder joint replacement implants. The present invention further relates to a device for collecting and retaining debris produced as a result of redressing a tapered portion, such as by the redressing device described herein. The invention is further directed to a method of redressing a tapered portion of an orthopaedic implant that includes use of one or more of the devices described herein.

In a first aspect there is provided a redressing device for redressing a tapered portion of an orthopaedic implant comprising:

a grinding member adapted to engage the tapered portion;

an adjustable guide element for defining, at least in part, the degree of redressing required for said tapered portion by a user;

a drive shaft for driving movement of said grinding member.

In one embodiment, the grinding member comprises a tapered recess at a distal end to facilitate engagement of the tapered portion therein. In an alternative embodiment, the grinding member comprises a nose portion that tapers in width from a proximal end to a distal end. Suitably, the tapered recess or the nose portion is substantially frusto-conical in shape.

In one embodiment, the guide element telescopes within at least a distal end portion of the drive shaft so as to be substantially coaxial therewith.

In one embodiment, the guide element comprises an axial channel extending through a longitudinal axis thereof and adapted to receive a flow of liquid therethrough.

Suitably, the grinding member comprises a plurality of grinding elements attached to a support and extending distally at an angle therefrom to define a tapered grinding zone therebetween. Preferably, the grinding member comprises at least three grinding elements. In certain embodiments, the grinding elements are spaced equidistant about an outer edge portion of the support. In particular embodiments, the grinding elements are substantially cylindrical in shape. The grinding elements are suitably rotatable and/or axially moveable about a longitudinal axis thereof by the drive shaft.

In one embodiment of the present aspect, the redressing device further comprises a housing for receiving the grinding member therein, the housing having an aperture at a distal end to receive the tapered portion therethrough. Suitably, the housing comprises:

an inlet communicating with said housing to facilitate the flow of liquid into said housing; and an outlet communicating with said housing to facilitate the flow of liquid out of said housing;

to facilitate cooling of the device during use.

In a second aspect there is provided a device for retaining debris produced during redressing a tapered portion of an orthopaedic implant comprising:

a membrane having an aperture for receiving the tapered portion therethrough; and a frame attached to the membrane and operable to maintain the membrane in an open configuration.

In one embodiment, the aperture is adapted to sealingly engage a neck portion adjacent the tapered portion.

In one embodiment, the device of the present aspect further comprises a resiliently deformable ring for sealingly engaging the aperture around a neck portion adjacent the tapered portion.

For the device of the present aspect, the frame is suitably deformable so as facilitate maintaining the membrane in the open configuration and/or to substantially conform to a surgical site.

In one embodiment, the membrane is or comprises a thin elastomeric sheet.

Suitably, the device is for use with the redressing device of the second aspect.

In a third aspect there is provided a surgical kit for redressing a tapered portion of an orthopaedic implant comprising:

(i) the redressing device of the first aspect; and
(ii) the device of the second aspect.

In a fourth aspect there is provided a method of redressing a tapered portion of an orthopaedic implant including the steps of:

(i) providing a redressing device comprising a grinding member adapted to engage the tapered portion, an adjustable guide element for defining, at least in part, a degree of redressing required for said tapered portion by a user, and a drive shaft for driving movement of said grinding member;
(ii) engaging the device with the tapered portion; and
(iii) redressing the tapered portion with the device.

Suitably, the redressing device is that of the first aspect.

In one embodiment, the method of the present aspect further includes the step of adjusting the adjustable guide element to a level suitable for the degree of redressing of the tapered portion required by the user.

In one embodiment, the method of the present aspect further includes the steps of:

(i) providing a device comprising a membrane having an aperture for receiving the tapered portion therethrough and a frame attached to the membrane and operable to maintain the membrane in an open configuration; and
(ii) sealingly engage the aperture around a neck portion adjacent the tapered portion.

Suitably, the device is that of the second aspect.

BRIEF DESCRIPTION OF THE DRAWINGS

In order that the present invention may be readily understood and put into practical effect, reference will now be made to the accompanying illustrations, wherein like reference numerals are used to refer to like elements.

DETAILED DESCRIPTION

FIGS. 1 through 7 demonstrate a number of embodiments of a device for redressing a tapered portion, including male and female configurations thereof, of an orthopaedic implant. It would be appreciated that these devices are for redressing a damaged tapered portion, preferably interoperatively, so as to facilitate engagement of a corresponding component, such as a new femoral head component, thereon and thereby maximise the contact area between the respective male and female tapered portions.

As would be appreciated by the skilled artisan, hip replacement components typically include an elongated femoral stem component, which is typically metallic and has a lower end to fit endwise into a corresponding recess formed in a femur and a neck portion that extends generally angularly from the upper end of the femoral stem component. An upper end portion of the femoral stem component typically includes a tapered portion, such as a tapered recess/bore or a tapered extension/nose (i.e., a trunnion), adapted to receive a corresponding tapered extension/nose or recess/bore respectively in a femoral head component of the orthopaedic implant. The femoral head component is generally metallic or ceramic and is of suitable dimensions to be received into a socket defined by the joint of interest.

When installed on the femoral stem component, the femoral head component is positioned to bear on either the patient's natural acetabulum or an acetabular component which has been implanted into the patient's pelvis to replace his or her acetabulum. In such a manner, the orthopaedic implant and the natural or artificial acetabulum collectively function as a system which replaces the natural joint of the patient's hip. To this end, the acetabular component may include an acetabular shell which comprises a tapered recess into which an acetabular liner of suitably dimensions typically matingly engages. It would be appreciated by the skilled artisan that the tapered recess of the acetabular component may also be redressed by one or embodiments of the device hereinafter described.

Figure 1:
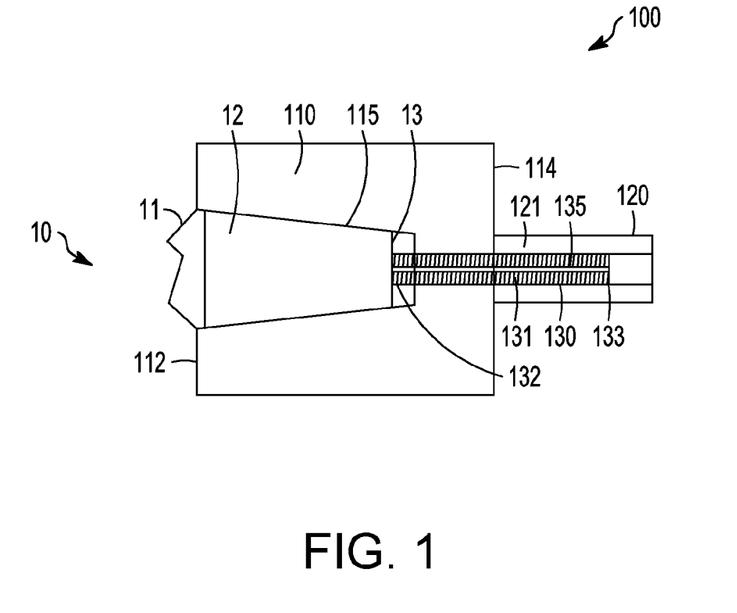
FIG. 1: is a central longitudinal section view of an embodiment of a device of the invention.

In FIG. 1, the device 100 includes a grinding member 110 which is of unitary structure having a tapered recess 115 opening at a distal end 112 thereof. In the embodiment provided, the tapered recess 115 is substantially frustoconical in shape (i.e., tapers in width from a distal end 112 to the proximal end 114) so as to matingly receive a substantially frustoconical tapered portion 12 of a femoral stem component 11 of an orthopaedic implant 10 therein.

As shown in FIG. 1, the tapered recess 115 of the device 100 has a first taper angle and a first taper diameter that substantially match a second taper angle and a second taper diameter along the length of the tapered portion 12 of the orthopaedic implant 10. It would be appreciated by the skilled artisan, that each orthopaedic implant's tapered portion 12 may vary depending, for example, on the size of the femoral stem component 11 and/or femoral head component (not shown) to be used. Typically, however, the tapered portion 12 of the femoral stem component 11 and the corresponding tapered portion of the femoral head component (not shown) are commonly sized across the range of component sizes, such that each of the differently-sized head components is generally compatible with each of the differently-sized femoral stem components 11.

With reference to the device of FIG. 1, a centrally located drive shaft 120 extends axially through a proximal portion 114 of the grinding member 110 and is operably attached thereto. An upper end of the drive shaft 120 is operably connected to and rotationally driven by an electric motor (not shown). When the motor is on, the drive shaft 120 rotates the grinding member 110 about a longitudinal axis of the device 100. In particular embodiments, the motor is or comprises a surgical drill (not shown), such as an orthopaedic surgical drill. To this end, the drive shaft 120 will suitably be functionally or operably connectable and/or connected to the surgical drill. By way of example, the connection may be a chuck or the like or a proprietary connection as are known in the art.

From FIG. 1, an adjustable guide element 130 having an elongate shank 131 including proximal and distal ends 133, 132 thereof, extends axially through the hollow shaft 121 of the drive shaft 120 such that the adjustable guide element 130 is coaxial with said drive shaft 120. The proximal end 133 of the adjustable guide element 130 further extends into the space or grinding zone defined by the tapered recess 115 to contact the tapered portion 12 at a flattened end portion 13 thereof. In the embodiment provided, the elongate shank 131 includes a plurality of external threads therealong that are screwingly engaged by the grinding member 110, such that the adjustable guide element 130 may be extended or retracted into a desired position within the space defined by the tapered recess 115 by rotational movement thereof by a user.

By way of example, if minimal redressing of the tapered portion 12 is required by a user, then the adjustable guide element 130 will be extended a greater distance into the space defined by the tapered recess 115 than if more significant redressing were required. Conversely, if more significant redressing of the tapered portion 12 is required, then the adjustable guide element 130 can then be screwingly retracted from the space defined by the tapered recess 115. To this end, the tapered portion 12 of the orthopaedic implant 10 upon operation of the device 100 is redressed by rotational and/or axial movement of the grinding member 110 thereon until the flattened end portion 13 thereof contacts the distal end 132 of the adjustable guide element 130. Once the adjustable guide element 130 is contacted by the tapered portion 12, further redressing thereof is substantially prevented or inhibited.

It may be possible to provide a tapered recess 115 in which the taper angle is adjustable, such that different tapered portions 12 can be redressed. This could, for example, be achieved by a constriction or expansion mechanism at either the proximal or distal end of the tapered recess 115 of the grinding member 110, which can adjust the taper angle thereof. This adjustment may only be very small, of the order of minutes or seconds for example, but may advantageously improve the utility of the device 100.

It would be appreciated that the adjustable guide element 130 may be configured to be movable relative to the grinding member 110, such as between an extended and retracted position, by other means as are generally known in the art. By way of example, in alternative embodiments, the shank 131 includes an automatic locking and release mechanism thereon for automatically locking the adjustable guide element 130 into a desired position as determined by a user.

In referring to the embodiment in FIG. 1, the adjustable guide element 130 further comprises a cannulated portion 135 extending axially along the length of the shank 131 for receiving a cooling fluid therethrough. It would be apparent to the skilled person that when grinding and/or redressing hard orthopaedic surfaces, such as a metallic implant or bone, a device would usually be employed together with water and/or other cooling fluids (e.g., saline). To this end, the cooling fluid acts to reduce the temperature at the contact area between the tapered portion 12 and the grinding member 110. The residual particles (i.e., debris from the redressed tapered portion 12) from the grinding or redressing process may also be collected together with the cooling fluid and removed from the grinding zone by said cooling fluid. Accordingly, the surgical drill which is connected to the drive shaft 120 may further be cannulated so as to provide fluids for the cannulated portion 135 of the adjustable guide element 130.

Figure 2:
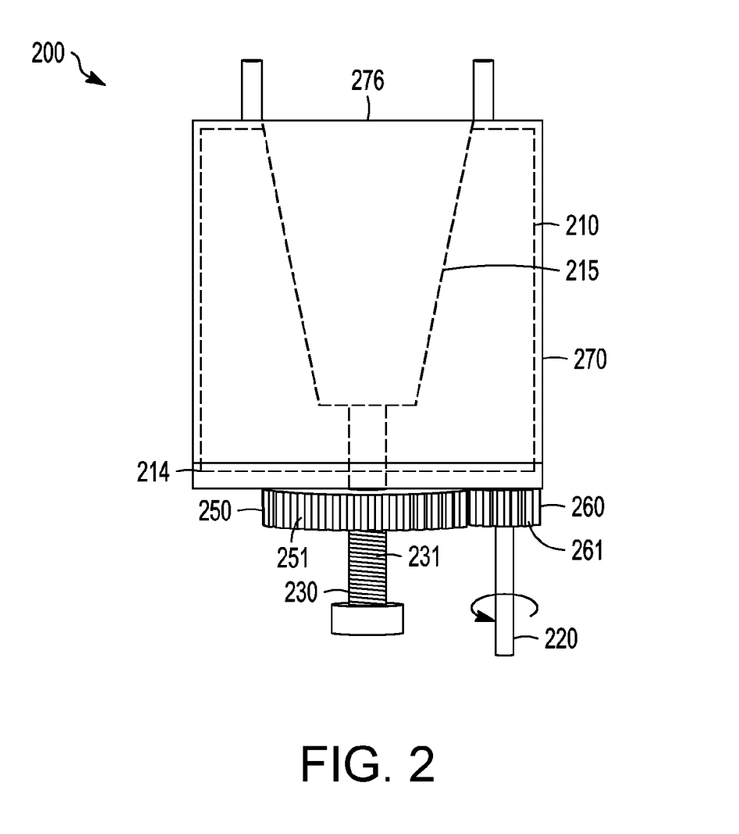
FIG. 2: is a side view of a further embodiment of a device of the invention.

FIG. 2 demonstrates another embodiment of a device 200, which provides an alternative arrangement of a drive shaft 220 and an adjustable guide element 230. The centrally located adjustable guide element 230 has an elongate shank 231 that extends axially through a sun gear 250 and a proximal portion 214 of the grinding member 210 and into a space defined by a tapered recess 215. The drive shaft 220 is located peripherally to the adjustable guide element 230 and extends axially along a longitudinal axis of the device 200 through a planet gear 260, to which the drive shaft 220 is functionally or operably attached, and a proximal portion 214 of the outer periphery of the grinding member 210. As can be observed in FIG. 2, the outer periphery of the sun gear 250 includes a plurality of gear teeth 251 formed thereon. Each of these gear teeth 251 include mating surfaces that engage with corresponding mating surfaces on respective gear teeth 261 of the planet gear 260. Accordingly, when the drive shaft 220 drives rotational movement of the planet gear 260, this in turn drives rotational movement of the sun gear 250 as well as the unitary grinding member 210 to which the sun gear 250 is functionally attached.

The device 200 further includes a housing 270 for housing the grinding member 210 therein. The housing also has an opening or aperture (not shown) at a distal end 276 of suitable dimensions for receiving the tapered portion 12 therethrough. It would be appreciated that the housing 270 may additionally comprises one or more inlets and/or outlets so as allow for the passage of fluids, such as that demonstrated in FIGS. 3 and 4 for the device 300.

Figure 3:
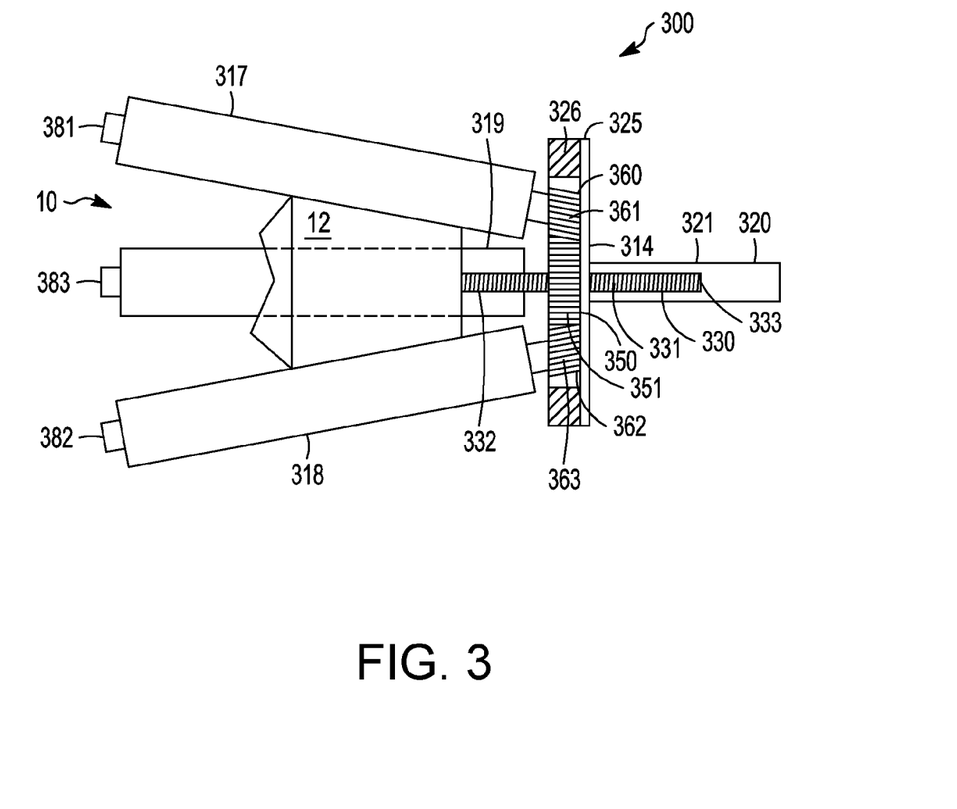
FIG. 3: is a side view of another embodiment of a device of the invention.

In FIG. 3, a further embodiment of a device 300 is provided. The device 300 includes three grinding elements 317, 318, 319 each attached to a support 325 and spaced equidistant around a peripheral portion 326 thereof. As can be seen in FIG. 3, the grinding elements 317, 318, 319 extend distally at an angle from the support 325 to define a space or grinding zone therebetween that is of suitable dimensions for receiving the frustoconical tapered portion 12 of the orthopaedic implant 10 therein.

Each of the grinding elements 317, 318, 319 is functionally or operably attached to a respective planet gear 360, 362, 364 which are located within a peripheral portion 326 of the support 325. It will be noted that the planet gear 364 for the grinding element 319 is not shown in FIG. 3. The outer periphery of the planet gears 360, 362, 364 include a plurality of respective gear teeth 361, 363, 365 that are formed thereon and have mating surfaces that engage with corresponding mating surfaces on respective gear teeth 351 of a sun gear 350. Accordingly, when the centrally located drive shaft 320 drives rotational movement of the sun gear 350, this in turn drives rotational movement of each of the planet gears 360, 362, 364 as well as their respective grinding elements 317, 318, 319 which are functionally or operably attached thereto.

In referring to FIG. 3, the device 300 further has a centrally located adjustable guide element 330, which includes an elongate shank 331 that extends axially through the hollow shaft 321 of the drive shaft 320, such that the adjustable guide element 330 is coaxial with said drive shaft 320. The adjustable guide element 330 further extends axially through a central portion of the support 325 and the sun gear 350 and into the space defined by the grinding elements 317, 318, 319. In the embodiment provided, the elongate shank 331 includes a plurality of external threads extending therealong that screwingly engage a central portion of the support 325, such that the adjustable guide element 330 may be extended or retracted into a desired position within the space defined by the grinding elements 317, 318, 319 by a user by rotational movement thereof. In alternative embodiments, it would be appreciated that the adjustable guide element 330 may be configured to be movable relative to the grinding elements 317, 318, 319, such as between an extended and retracted position, by any means known in the art, such as those hereinbefore described. The relative positioning of the grinding elements 317, 318, 319 could also be adjusted in order to provide adjustability to the taper angle of the device 300. This could be achieved, for example, by providing lockable joints for each grinding element 317, 318, 319 preferably at or adjacent to their respective planet gears 360, 362, 364, so as to allow for adjustment of the angular relationship therebetween.

Although not shown in FIG. 3, it would be apparent that the adjustable guide element 330 may further include a cannulated portion extending axially along the length of the shank 331 for receiving a cooling fluid therethrough, similar to that demonstrated in FIG. 1 for device 100. Additionally, the device 300 may further comprise a housing (not shown), such as that described herein. To this end, the device 300 includes supporting elements 381, 382, 383 at a respective distal end of each of the grinding elements 317, 318, 319. The supporting elements 381, 382, 383 may be adapted for receiving and engaging a housing (not shown) thereon. Additionally or alternatively, the supporting elements 381, 382, 383 may be configured for engaging or supporting an engagement member (not shown), such as that provided for device 400, so as facilitate stabilisation of the grinding elements 317, 318, 319 together with the tapered portion 12 of the orthopaedic implant 10 when device 300 is in use.

Figure 4:
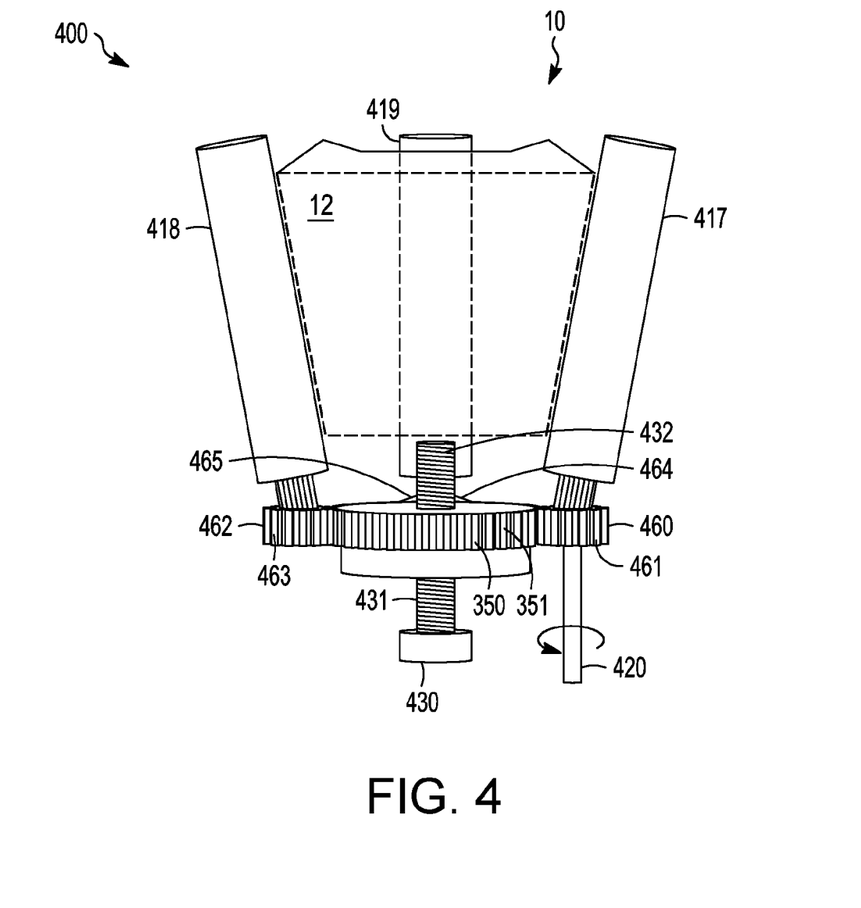
FIG. 4: is a side view of yet another embodiment of a device of the invention.
Figure 5:
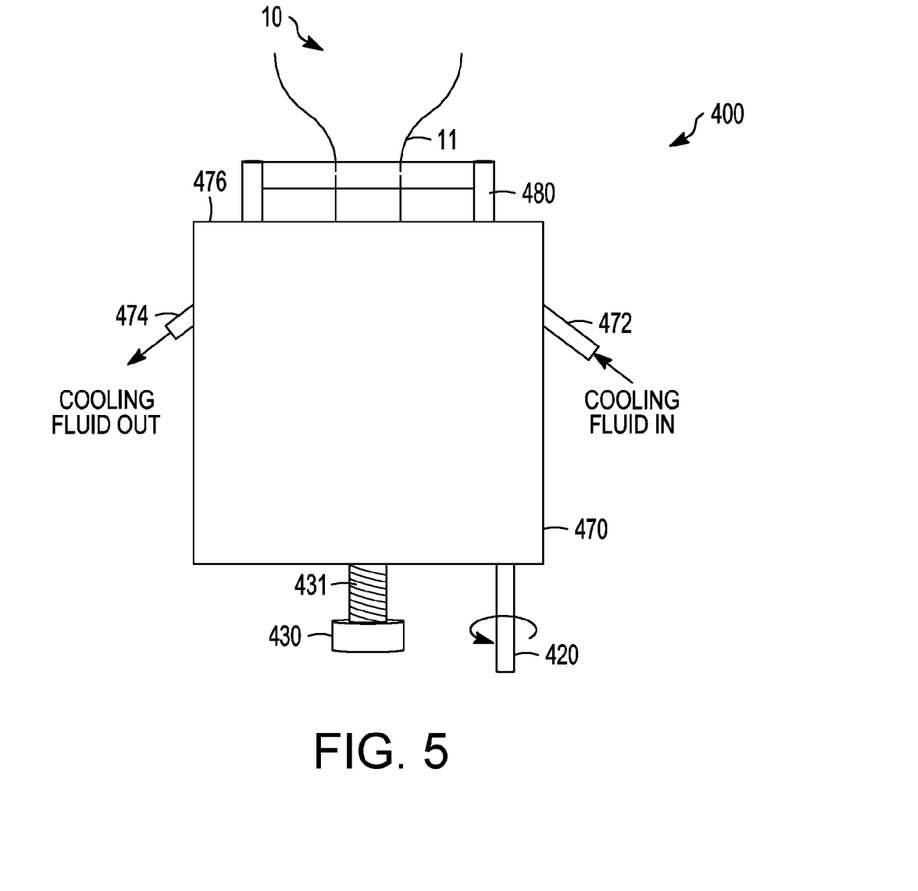
FIG. 5: is a side view of the device of FIG. 4.

FIGS. 4 and 5 provide a further embodiment of a device 400. The device 400 includes three grinding elements 417, 418, 419 that are functionally attached or connected to a respective planet gear 460, 462, 464, which are spaced equidistant within a peripheral portion of a support (not shown). As can be observed from FIG. 4, the grinding elements 417, 418, 419 extend distally at an angle from their respective planet gear 460, 462, 464 to define a space therebetween that is of suitable dimensions for receiving the frustoconical tapered portion 12 of the orthopaedic implant 10 therein.

Although FIG. 4 shows only three grinding elements 417, 418, 419, it is clear that the device 400 may employ four or even more such elements (e.g., 5, 6, 7 etc grinding elements) in order to ensure rapid and accurate redressing of the contact surfaces of the tapered portion 12. These grinding elements could also be relatively angularly adjustable in order to provide some adjustment of the taper angle of the device 400.

As can be seen in FIG. 4, the device 400 has a drive shaft 420 located peripherally to a centrally positioned adjustable guide element 430 and extending axially along a longitudinal axis of the device 400 to functionally or operably attach to a planet gear 460. The outer periphery of the planet gear 460 includes a plurality of gear teeth 461 formed thereon. Each of these gear teeth 461 includes mating surfaces that engage with corresponding mating surfaces on respective gear teeth 451 of a sun gear 450. The gear teeth 451 of the sun gear 450 further engage with corresponding mating surfaces on respective gear teeth 463, 465 of planet gears 462, 464. Accordingly, when the drive shaft 420 drives rotational movement of the planet gear 460, this in turn drives rotational movement of the sun gear 450 as well as the planet gears 462, 464 so as to drive rotation of the grinding elements 417, 418, 419 functionally or operably attached thereto.

Referring to FIG. 5, the device 400 further includes a housing 470 for housing the grinding elements 417, 418, 419 therein. The housing also has an opening or aperture (not shown) at a distal end 476 of suitable dimensions for receiving the tapered portion 12 therethrough. In the embodiment provided, the housing 470 is removably attached to the device 400 so as to allow for easy cleaning thereof.

As can be seen from FIG. 5, the housing 470 further includes an inlet 472 and an outlet 474 both in fluid communication with the housing so as to facilitate a flow of a cooling fluid into and out of said housing 470 respectively. It would be appreciated that such an arrangement or similar allows for cooling of the device 400 during use as well as promote the removal, at least partly, of any debris produced during redressing of the tapered portion 12.

The device 400, as illustrated in FIG. 5, further comprises an engagement member 480 extending distally from a distal end 476 of the housing 470 and adapted to reversibly engage the femoral neck component 11 of the orthopaedic implant 10. To this end, the engagement member 480 when in use preferably stabilises engagement of the device 400, and more specifically the grinding elements 417, 418, 419, together with the tapered portion 12 of the orthopaedic implant 10.

Figure 6:
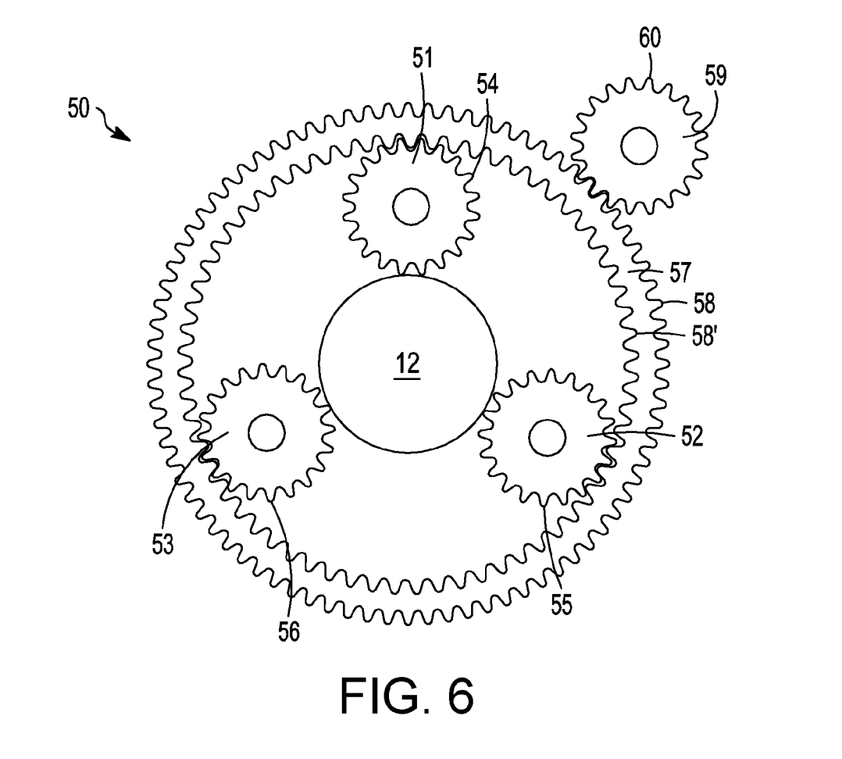
FIG. 6: is a top view of a gear arrangement for use in an embodiment of a device of the invention.

FIG. 6 demonstrates an alternative embodiment of a gear arrangement 50 that may be suitable for use with, for example, the devices 300, 400 previously described herein. As can be seen in FIG. 6, the gear arrangement 50 has a drive gear 59 located peripherally to a centrally positioned ring gear 57. Although not shown in FIG. 6, the drive gear 59 is to functionally or operably attach to a drive shaft. The outer periphery of the drive gear 59 includes a plurality of gear teeth 60 formed thereon that engage with corresponding gear teeth 58 on the outer periphery of the ring gear 57. The inner periphery of the ring gear further includes gear teeth 58', which engage with corresponding mating surfaces on respective gear teeth 54, 55, 56 of planet gears 51, 52, 53. The planet gears 51, 52, 53 are each to be operably attached to a separate grinding element (not shown), such as shown for devices 300, 400. Accordingly, when the drive shaft (not shown) drives rotational movement of the drive gear 59, this in turn drives rotational movement of the ring gear 57 as well as the planet gears 51, 52, 53 so as to drive rotation of the grinding elements (not shown) that are functionally attached thereto.

Figure 7:
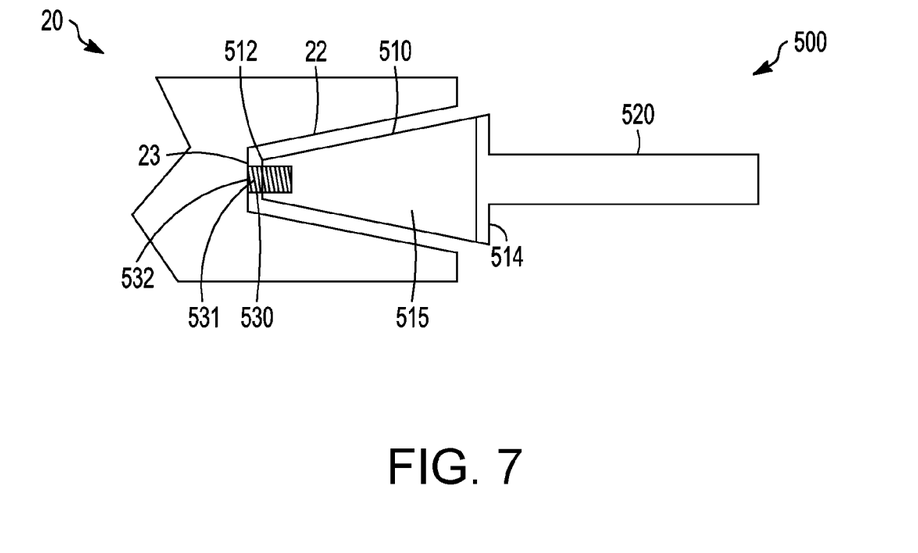
FIG. 7: is a central longitudinal section view of a further embodiment of a device of the invention.

FIG. 7 demonstrates an embodiment of a device 500 for redressing a tapered recess 22 of an orthopaedic implant 20. In this regard, the tapered recess 22 may be part of, for example, either a femoral stem component, a femoral head component or an acetabular component of the orthopaedic implant 20. The device 500 includes a grinding member 510 which is of unitary structure having a tapered nose portion 515 tapering in width from a proximal end 514 to a distal end 512 thereof. To this end, the tapered nose portion 515 is substantially frustoconical in shape and of suitable dimensions so as to be matingly received into the substantially frustoconical tapered recess 22 of the orthopaedic implant 20.

In reference to FIG. 7, the device 500 further includes a centrally located drive shaft 520 that attaches to a proximal portion 514 of the grinding member 510. An upper end of the drive shaft 520 is rotationally driven by an electric motor (not shown). When the motor is on, the drive shaft 520 rotates the grinding member 510 about a longitudinal axis of the device 500. The motor may be that as described herein (e.g., a cannulated surgical drill). Additionally, the device 500 may further comprise a housing (not shown), such as that described herein for devices 100, 200, 300, 400.

The device 500 further has an adjustable guide element 530, which includes a threaded elongate shank 531 that is matingly engaged with the distal end 531 of the tapered nose portion 515 and extends distally and outwardly therefrom. In the embodiment provided, the adjustable guide element 530 is coaxial with the drive shaft 520. By virtue of the aforementioned external threads extending along the elongate shank 531, the adjustable guide element 530 may be extended or retracted into a desired position extending from the tapered nose portion 515 and into the space defined by the tapered recess 22 by rotational movement thereof. It would be appreciated that the adjustable guide element 530 may alternatively be configured to be movable relative to the tapered nose portion 515 by any means known in the art, including those hereinbefore described.

With respect to the adjustable guide element 530, if minimal or minor redressing of the tapered recess 22 is required by a user, then the adjustable guide element 530 may be extended a greater distance into the space defined by the tapered recess 22 than if more significant redressing were required. Conversely, if more significant redressing of the tapered recess 22 is required, then the adjustable guide element 530 can then be screwingly retracted from the tapered recess 22 into the tapered nose portion 515. To this end, the tapered recess 22 is redressed for removal of, for example, any fretting or corrosion therein, by rotational movement of the tapered nose portion 515 of the grinding member 510 therein until the flattened base portion 23 of the tapered recess 22 contacts the distal end 532 of the adjustable guide element 530. Once the adjustable guide element 530 contacts the flattened base portion 23 of the tapered recess 22, further redressing thereof is substantially prevented or inhibited.

With respect to the embodiments provided in FIGS. 1 through 7, it would be appreciated that the rotational speed and/or the direction of rotation of the grinding member or grinding elements are preferably variable, such as by employing a reversible motor or a surgical drill including a reversible motor. Such an arrangement may assist in regulating, for example, the amount of fretting and/or corrosion removed from the contact surfaces of the tapered portion or recess of the orthopaedic implant during use of such devices. It would also be apparent that in addition or alternatively to rotational movement, the grinding member or grinding elements may also be configured to perform axial movement, or the like, relative to a longitudinal axis thereof.

Figure 8:
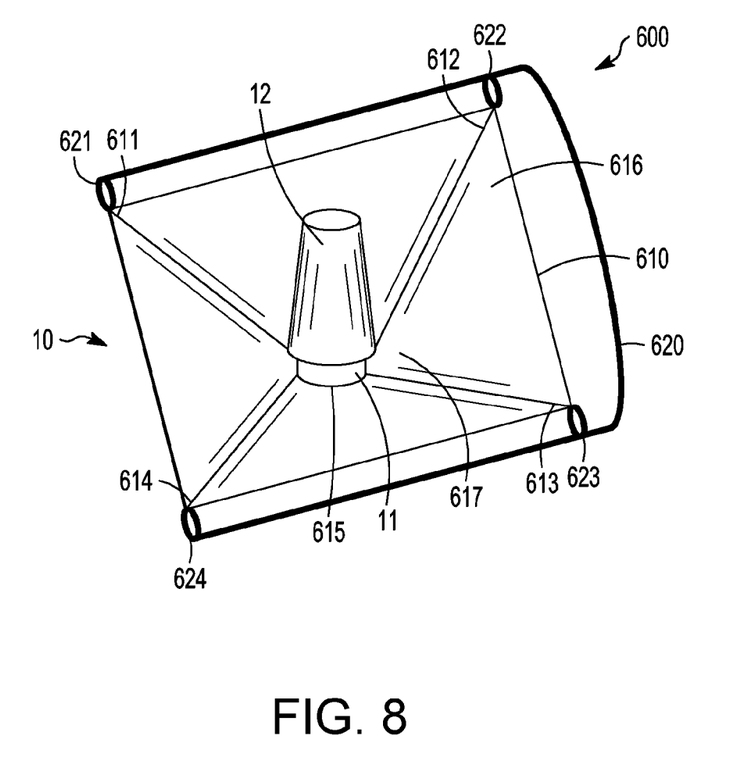
FIG. 8: is a perspective view of an alternative embodiment of a device of the invention.

In FIG. 8, an embodiment of a device 600 for use during redressing of a tapered portion 12. The device 600 includes a membrane 610 and a frame 620. The membrane 610 comprises a central and thin elastomeric sheet that may include materials, such as rubber, plastic, silicone, latex or combinations thereof. Further, the membrane 610 is preferably substantially non-porous so as to facilitate the collection and retainment of, at least in part, any fluids and/or solid materials or debris produced as a result of a taper redressing procedure therein. The debris and fluids collected in the membrane 610 may subsequently be removed by a suction device as required. Suitably, the membrane 610 is of dimensions to substantially cover a surgical site during, for example, revision surgery for a failed orthopaedic implant. By way of example, the membrane 610 is preferably square or rectangularly shaped, with, for example, 10 to 20 cm sides.

As can be observed in FIG. 8, the membrane 610 and frame 620 are formed separately, but are joined together by four hooks or loops 621, 622, 623, 624 which each engage a respective corner portion 611, 612, 613, 614 of the membrane 610 so as to be maintained in an extended or open configuration. It would be appreciated that alternative means of attaching the membrane 610 and the frame 620 as are known in the art may be utilised, such as with a suitable adhesive, or by other means of attachment as are generally known in the art.

The membrane 610 includes an upper portion 616 and a lower portion 617, the lower portion 617 further including an aperture 615 of suitable dimensions to receive therethrough the tapered portion 12 and subsequently sealingly engage the femoral neck component 11 of the orthopaedic implant 10. Although not shown in FIG. 6, the device 600 may further include an elastic ring or the like to assist in sealingly engaging the lower portion 617 of the membrane 610 around the tapered portion 12 that is to be redressed when in use. In view of this arrangement, it would be appreciated that the device 600 would substantially prevent objects, such as debris and fluids produced as a result of redressing the tapered portion 12 from entering the patient's surgical site, by collecting and retaining such objects via the membrane 610.

The device 600 may be sealingly engaged to the femoral neck component 11 of the orthopaedic implant 10 by any means known in the art. In particular embodiments, the device 600 is sealingly engaged to the femoral neck component 11 by pliers, such as elastrator pliers, or a pronged tool, such as a haemostat or modified haemostat. In one embodiment, the pronged tool, such as four-pronged elastrator pliers, may be used to radially stretch the aperture 615 to suitable dimensions to be placed over the tapered portion 12. In another example, a haemostat may be used to radially stretch the aperture 615 by inserting and opening the distal ends of the haemostat therein.

It will be readily appreciated that the device 600 of this invention may be disposable after a single use, or alternatively may be subsequently sterilised and re-used. In particular embodiments, the frame 620 is adapted to be reusable (i.e., sterilisable, autoclavable etc), whilst the membrane 610 is adapted for single use only. The device 600 can be individually packaged in a sterile package thereby eliminating the need to sterilize the components prior to revision surgery.

In this specification, adjectives such as first and second, and the like may be used solely to distinguish one element or action from another element or action without necessarily requiring or implying any actual such relationship or order. Words such as "comprises" or "includes" are intended to define a non-exclusive inclusion, such that a method or apparatus that comprises a list of elements does not include only those elements but may include other elements not expressly listed, including elements that are inherent to such a method or apparatus.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

REFERENCES

1. Banerjee, S., et al., Gross trunnion failure after primary total hip arthroplasty. J Arthroplasty, 2015. 30(4): p. 641-8.
2. Lavernia, C. J., et al., Trunnion-Head Stresses in THA: Are Big Heads Trouble? J Arthroplasty, 2015. 30(6): p. 1085-8.
3. Pastides, P. S., et al., Trunnionosis: A pain in the neck. World J Orthop, 2013. 4(4): p. 161-6.
4. Porter, D. A., et al., Modern trunnions are more flexible: a mechanical analysis of THA taper designs. Clin Orthop Relat Res, 2014. 472(12): p. 3963-70.

The invention claimed is:

1. A redressing device to redress a tapered portion of an orthopaedic implant comprising:
   a grinding member having a tapered recess adapted to engage the tapered portion;
   an adjustable guide element which is extendable or retractable within the tapered recess
   to adjustably engage said tapered portion and limit axial movement thereof with respect
   to the grinding member, thereby defining, at least in part, the degree of redressing required of said tapered portion by a user; and
   a drive shaft to drive movement of said grinding member.

2. The redressing device of claim 1, wherein the grinding member comprises a nose portion that tapers in width from a proximal end to a distal end.

3. The redressing device of claim 1, wherein the guide element telescopes within at least a distal end portion of the drive shaft so as to be coaxial therewith.

4. The redressing device of claim 1, wherein the guide element comprises an axial channel extending through a longitudinal axis thereof and adapted to receive a flow of liquid therethrough.

5. The redressing device of claim 1, wherein the grinding member comprises a plurality of grinding elements attached to a support and extending distally at an angle therefrom to define a tapered grinding zone therebetween.

6. The redressing device of claim 5, wherein the grinding elements are at least one of:
   spaced equidistant about an outer edge portion of the support; and
   cylindrical in shape.

7. The redressing device of claim 5, wherein the grinding elements are adapted to rotate and/or axially move about a longitudinal axis thereof by the drive shaft.

8. The redressing device of claim 1, further comprising a housing to receive the grinding member therein, the housing having an aperture at a distal end to receive the tapered portion therethrough, wherein the housing comprises:
   an inlet communicating with said housing to facilitate the flow of liquid into said housing; and
   an outlet communicating with said housing to facilitate the flow of liquid out of said housing to facilitate cooling of the device during use.

9. The redressing device of claim 1, wherein the grinding member is of a single unitary structure, and the tapered recess is frustoconical in shape and tapers in width from a distal end to a proximal end.

10. The redressing device of claim 9, wherein the tapered recess defines an opening in the grinding member at a distal end thereof.

* * * * *